United States Patent [19]
Shimmick

[11] Patent Number: 6,056,740
[45] Date of Patent: *May 2, 2000

[54] METHOD AND APPARATUS FOR COMBINED CYLINDRICAL AND SPHERICAL EYE CORRECTIONS

[75] Inventor: John K. Shimmick, Redwood City, Calif.

[73] Assignee: Visx, Incorporated, Sunnyvale, Calif.

[*] Notice: This patent is subject to a terminal disclaimer.

[21] Appl. No.: 08/841,001

[22] Filed: Apr. 18, 1997

Related U.S. Application Data

[63] Continuation of application No. 08/698,971, Aug. 16, 1996, abandoned, which is a continuation of application No. 08/138,552, Oct. 15, 1993, Pat. No. 1,713,892, which is a continuation of application No. 07/746,446, Aug. 16, 1991, abandoned.

[51] Int. Cl.⁷ ..................................................... A61N 5/06
[52] U.S. Cl. ..................................... 606/5; 606/3; 606/10
[58] Field of Search ......................................... 606/2, 3–6

[56] References Cited

U.S. PATENT DOCUMENTS

| | | |
|---|---|---|
| 3,330,182 | 7/1967 | Gerber et al. . |
| 3,710,798 | 1/1973 | Bredemeir . |
| 3,769,963 | 11/1973 | Goldman et al. . |
| 3,828,188 | 8/1974 | Kraskow et al. . |
| 3,982,841 | 9/1976 | L'Esperance . |
| 4,170,997 | 10/1979 | Pinnow et al. . |
| 4,173,980 | 11/1979 | Curtin . |
| 4,266,548 | 5/1981 | Davi . |
| 4,309,998 | 1/1982 | Rosa et al. . |
| 4,409,979 | 10/1983 | Rousset et al. . |
| 4,461,294 | 7/1984 | Baron . |
| 4,485,499 | 12/1984 | Castelman . |
| 4,538,608 | 9/1985 | L'Esperance . |
| 4,665,913 | 5/1987 | L'Esperance . |
| 4,669,466 | 6/1987 | L'Esperance . |
| 4,686,979 | 8/1987 | Gruen et al. . |

(List continued on next page.)

FOREIGN PATENT DOCUMENTS

| | | |
|---|---|---|
| 0296982 | 12/1988 | European Pat. Off. . |
| 0346116 | 12/1989 | European Pat. Off. . |
| 2626466 | 4/1989 | France . |
| WO/91/11158 | 8/1991 | WIPO . |

OTHER PUBLICATIONS

Deposition of Dr. Rangaswamy Srinivasan, p. 27 (lines 8–20, Jan. 16, 1990 (Interference No. 102,026, Trokel v. L'Esperance).

Affidavit of Louis J. Girard, (United States application Serial No. 891,169 to L'Esperance, executed Dec. 2, 1987).

*Myopia Surgery,* McMillan Publishing Co, Inc., New York, Toronto, London, Chapter 5 by W. Andrew Maxwell and Lee T. Nordan entitled "Myopic Keratomileusis," (1990) pp. 129–134.

*Ophthalmologie,* Louis Guillaumat, pp. 344 and 346 entitled "Pathologie Regionale Et Tissuelaire," publication date 1953.

(List continued on next page.)

*Primary Examiner*—David M. Shay
*Attorney, Agent, or Firm*—Oblon, Spivak, McClelland, Maier & Neustadt, P.C.

[57] ABSTRACT

A method for performing concurrent spherical and cylindrical corrections to the corneal surface of the eye to reduce myopia and astigmatism. A laser beam irradiates the corneal surface via a variable diameter iris and a slot produced by a pair of translatable blades. The width of the slot and the diameter of the iris are varied as the laser is pulsed to produce a toric ablation of the corneal surface. Alternatively, the laser beam is passed through a succession of apertures in a tilted variable aperture element to produce toric ablation. The total number of laser pulses required to effect both types of correction is equal to the number required for the spherical correction alone, reducing the laser power and the procedure time. The toric ablation produces no steep end walls as with standard cylindrical ablation procedures, thereby eliminating hyperopic shift and minimizing flattening along the ablated cylinder axis.

61 Claims, 2 Drawing Sheets

U.S. PATENT DOCUMENTS

| | | |
|---|---|---|
| 4,688,201 | 8/1987 | Towner et al. . |
| 4,729,372 | 3/1988 | L'Esperance . |
| 4,732,148 | 3/1988 | L'Esperance . |
| 4,744,360 | 5/1988 | Bath . |
| 4,768,874 | 9/1988 | Webb et al. . |
| 4,769,963 | 9/1988 | Goldman et al. . |
| 4,770,172 | 9/1988 | L'Esperance, jr. . |
| 4,773,414 | 9/1988 | L'Esperance . |
| 4,784,135 | 11/1988 | Blum et al. . |
| 4,825,865 | 5/1989 | Zelman . |
| 4,838,266 | 6/1989 | Koziol et al. . |
| 4,846,172 | 7/1989 | Berlin . |
| 4,911,711 | 3/1990 | Telfair et al. . |
| 4,941,093 | 7/1990 | Marshall et al. ................. 606/11 |
| 4,973,330 | 11/1990 | Azema et al. . |
| 4,994,058 | 2/1991 | Raven et al. . |
| 5,103,074 | 4/1992 | Watanabe et al. . |
| 5,395,356 | 3/1995 | King et al. . |
| 5,411,501 | 5/1995 | Klopoleh ........................ 606/5 |
| 5,423,801 | 6/1995 | Marshall et al. . |
| 5,461,212 | 10/1995 | Seiler et al. . |
| 5,713,892 | 2/1998 | Shimmich ........................ 606/5 |

OTHER PUBLICATIONS

"Lesion Duration and Curvature change in the Cornea Following Exposure to a Carbon Dioxide Laser," Mikesell et al., Report SAM–TR–79–26 (1979).

"Reshaping the Cat Corneal Anterior Surface Using a High–Speed Diamond Fraise," Olson et al.; Ophthalmic Surgery, (1980) pp. 784–786.

"Refractive Keratoplasty—Microkeratome Evaluation," Binder et al., Arch Ophthalmol., vol. 100, (1982), pp. 802–806.

"Excimer Lasers in Medicine," David Muller; Lasers & Applications (1986) pp. 85–89.

"Laser Shaping of Cornea Shows Promise at Correcting Eyesight," Jerry E. Bishop; Wall Street Journal, Technology Section, Jan. 30, 1987.

Reprint from Laser Surg. Med., 6, 241, 1986, abstract entitled "Corneal surgery with an ER:YAG Laser at 2.94 um., " Wolbarsht et al.

"Photoablative Reprofiling of the Cornea Using an Excimer Laser: Photorefractive Keratectomy," Marshall et al.; Lasers in Ophthalmology, vol. 1 No. 1 (1986), pp. 21–48.

"Quantitation of Corneal Ablation by Ultraviolet laser Light," Krueger et al.; Arch Ophthalmol. vol. 103, (1985), pp. 1741–1742.

"Guest Editorial: Excimer lasers in Ophthalmology," Steiner et al.; J. Cataract. Refract. Surg., vol. 15, (1989) pp. 369–370.

"Safety Fears Focused on 'healing' Laser," Jeff Hecht; New Scientisit, vol. 134, No. 1825, Technology Section, Jun. 13, 1992, p. 18.

Statutory Declaration of Professor John Marshall, prepared in connection with an Opposition by Summit Technology, Inc. to European patent No. 0 218 427, and executed on Sep. 17, 1993.

Statutory Declaration of Professor Carmen A. Puliafito, prepared in connection with an Opposition by Summit Technology, Inc. to European patent No. 0 218 427, and executed on Aug. 30, 1993.

Statutory Declaration of Professor Dr. Theo Seiler, prepared in connection with an Opposition by Summit Technology, Inc. to European patent No. 0 218 427, and executed on Aug. 5, 1993.

"Photorefractive Keratectomy (PRK)" Excimer Laser and Radial Keratotomy; World Wide Web page http://www.m-dweb.com/uslaser/prk.htm; (2 pages).

"The PRK Experience", Maddox Excimer Laser Center PRK Brochure at World Wide Web page http://www.excimernet.com/MPRKbody.htm; (22 pages).

Affidavit of Stephen L. Trokel, prepared in connection with opposition to European application No. 86307420.9–2305/0218427 and 87306826.6–2302/0257836, and executed on Dec. 5, 1995.

"Beyond Glasses!," Armstrong et al.; UC Books (1997), Title page and copyright page, pp. 4 and 5.

Printout of a database search on LEXIS for articles citing the Dec. 15, 1983 Trokel et al. article.

Apr. 20, 1998 letter from Jan Wetzel La Vigne to Mr. Larry Woody at VISX Corporation.

"Excimer Lasers in Ophthalmology", McGhee et al., Butterworth–Heinemann press, 1997, copy of the title page, the copyright page, and the table of contents pages.

"Laser Interactions With the Cornea," Krauss et al.; Survey of Ophthalmology, vol. 31, No. 1, Jul–Aug. (1986), pp. 37–53.

"An Acute Light and Electron Microscopic Study of Ultraviolet 193–nm Excimer Laser Corneal Incisions," Berns et al., Ophthalmology, vol. 95, No. 10, (1988), pp. 1422–1433.

"Excimer Laser Radial Keratectomy in the Living Human Eye: A Preliminary Report," Tenner et al., Journal of Refractive Surgery, vol. 4, No. 1, (1988), pp. 5–8.

"In Vivo Experiments With the Excimer Laser—Technical Parameters and Healing Processes," Seiler et al.; Ophthalmologica, vol. 192 (1986), pp. 65–70.

"Wound Healing Following Excimer Laser Radial Keratectomy," Rosa et al.; J. Cataract. Refract. Surg., vol. 14 (1988), pp. 173–179.

Interim Report entitled "Ocular Effects of Ultraviolet Laser Radiation," Joseph Zuclich, Report No. SAM–TR–74–32 (1974).

"Quantitative and Ultrastructural Studies of Excimer laser Ablation of the Cornea at 193 and 248 Nanometers," Puliafito et al.; Lasers in Surgery and Medicine, vol. 7 (1987), pp. 155–159.

Final Report entitled "Corneal Damage Thresholds for Hydrogen Flouride and Deuterium Fluoride Chemical Lasers," Irving L. Dunsky, et al.; Report No. SAM–TR–73–51 (1973).

"Human Excimer Laser Keratectomy: Short–Term Histopathology," L'Esperance et al.; Journal of Refractive surgery, vol. 4, No. 4 (1988), pp. 118–124.

"Traumatic Corneal Abrasions Following Photorefractive Keratectomy," James J. Salz; Refractive and Corneal Surgery, vol. 10, (1994), pp. 36–37.

"The Ultrastructure of Well–Healed Lenticles in Keratomileusis," Yamaguchi et al.; Dec. 1983, 90 (12) p. 1495–506, ISSN 0161–6420 (Dialog).

"Carbon Dioxide Laser Beam Control for Corneal Surgery," Richard Keates et al.; Ophthalmic Surgery vol. 12, No. 2 (1981), pp. 117–122.

"Biomechanical Study of Corneal Stability After Photorefractive Keratectomy," A. Bohm et al.; Feb. 1997, 94 (2) p. 10–9–13, ISSN 0941–293X (Dialog).

"An Experiment Study of the Possibility of Using Carbon Dioxide Laser for Changing the Cornea Refraction," SE Avetisov et al.; Vestnik Oftalmologii, 1982, N5, P32 (Dialog).

Declaration of Dr. Myron L. Wolbarsht, in support of the party L'Esperance's First, Second and Third Motions (Interference No. 102,026, executed Mar. 3, 1989).

U.S. Department of Commerce, Paper No. 102 entitled "Decision on Preliminary Motions" (Interference No. 102, 026).

"Cytotoxicity and Mutagenicity of Low Intensity, 248 and 193 nm Excimer laser Radiation in Mammalian Cells," H. Green et al., Cancer Research, vol. 47 (1987), pp. 410–413.

"Mutagenic Potential of a 193–nm Excimer Laser on Fibroblasts in Tissue Culture," J. Trentacoste et al.; Ophthalmology, vol. 94, No. 2 (1987), pp. 125–129.

"Unscheduled DNA Synthesis in Human Skin After In Vitro Ultraviolet–Excimer laser Ablation," H. Green et al.; Journal of Investigative Dermatology, vol. 89, No. 2 (1987), pp. 201–204.

"Human Excimer Laser Lamellar keratectomy," D. Taylor et al.; Ophthalmology, vol. 96, No. 5 (1989), pp. 654–664.

"Ocular Damage Induced By Near Ultraviolet Laser Radiation," Zuclich et al., Investigative Ophthalmology, *Reports,* vol. 15, No. 9 (1976), pp. 760–764.

Printout of IBM patent server web page citing 13 United States patents that reference United States patent No. 5,108, 388.

Printout of IBM patent server web page citing 26 United States patents that reference "Trokel et al." and "1983", the indicia identifying the seminal Trokel et al. 1983 publication.

"Lamellar Keratoplasty," Barraquer, JI; Ann. Ophthalmol (U.S.) Jun. 1972, 4(6) pp. 437–469, ISSN 0003–4886 (Dialog).

"Modification of Refraction by Means of Intracorneal Inclusions," Barraquer, JI; Int. Ophthalmol Clin. (U.S.) Spring 1966, 6(1) p53–78, ISSN 0020–8167 (Dialog).

Statement of Dr. Reinhardt Thyzel, prepared in connection with VISX Incoporated v. Nidek Co., Ltd. In the High Court of Justice, Chancery Division, England, CH 1996 V No. 7408; executed Nov. 7, 1998.

"Basis of Refractive Keratoplasty" by Barraquer, Arch. Soc. Offal. Optom (1967), pp. 21–68, except for pp. 22 and 42.

DE 3148748 A1 (German patent publication to Karp) (twelve pages).

English language translation of DE31 48 748 A1 to Karp (ten pages).

Interview Summary in the parent application for the Aug. 16, 1996 interview.

Title page, copyright page, and p. 1410 of the Dictionary of Scientific and Technical Terms, second edition.

Title page, copyright page, and p. 1286 of Dorland's Illustrated Medical Dictionary.

"Ocular Effects of a 325 Nm Ultraviolet Laser", Ebbers, et al., *American Journal of Optometry and Physiological Optics,* Mar. 1975 pp. 216–223.

"Thresholds And Mechanisms of Retinal Damage From a White–light Laser", Reed et al., *Health Physics,* Jul., 1980, pp. 33–39.

"Modification of Rabbit Corneal Curvature with Use of Carbon Dioxide Laser Burns," Gholam A. Peyman et al.; 11 Opthalmic Surgery, May 1980, pp. 325–329.

"Retinal Tissue Damage Induced by 6–psec 530–nm Laser Light Pulses", Bruckner et al., *Applied Optics,* Feb. 1982, pp. 365–367.

"Ocular Tissue Damage Due to Ultrashort 1060–nm Light Pulses from a Mode–locked Nd:glass Laser", Taboada et al., *Applied Optics,* Aug. 1975, pp. 1759–1761.

"Ocular Hazard from UV Laser Exhibiting Self–mode–locking", Zuchlich et al., *Applied Optics,* May 1978. pp. 1482–1484.

"Production of Cataracts in Rabbits with the Ultraviolet Laser", MacKeen et al., *Ophthal. Res.* 1973, pp. 317–324.

Taboada v. Trokel–CA No. SA97CA0794, filed Jul. 2, 1997—Complaint to Order Correction of Patent and For Other Relief.

Copy of office action mailed Apr. 13, 1998 for application serial No. 08/480,233.

A copy of the 37 C.F.R. 1.131 declaration of Dr. Stephen Trokel.

"Carbon Dioxide Laser Beam Control for Corneal Surgery", Keates et al. dated Feb., 1981 (DE 38 48 748) pp. 84 and 107–171 from vol. 2 of "Corneal Surgery" by Girard et al., published in 1981; w/English translation.

"Excimer Laser Surgery of the Cornea," Stephen Trokel et al.; pp. 710–715, American Journal of Ophthalmology, vol. 96, No. 6, Dec. 1983.

"An Extreme Sensitivity in the Corneal epithelium to Far UV Arf Excimer Laser Pulses"; Taboada et al., Proc. of the Scientific Program Aerospace Medial Association, 1981 meeting pp. 98–99.

"Response to the Corneal Epithelium to KrF Excimer Laser Pulses" by Taboada et al.; Health Physics vol. 40, May 1981, pp. 677–683.

Rebuttal Expert Report of Dr. Michael S. Feld Re: Validity; Civil Action No. 95–524–SLR; United States District Court for the District of Delaware; Dec. 30, 1996.

Report of James H. Brannon Pursuant to Federal Rule of Civil Procedure 26; Civil Action No. 95–524 SLR; United States District Court for the district of Delaware; Dec. 9, 1996.

Rebuttal Expert Report of Dr. Jack Feinberg Re: Validity; Civial Action No. 95–524–SLR; United States District Court for the District of Delaware; Dec. 23, 1996.

Deposition of Alain Azema; civil Action No. 95–524–SLR; United States District Court for the District of Delaware; Sep. 17, 1996.

Rebuttal Expert Report of Roger F. Steinert, M.D. Re: Validity; Civil Action No. 95–524–SLR; United States District Court for the District of Delaware; Dec. 30, 1996.

Facsimile letter dated Jun. 7, 1994 from Howard L. Milhench, attorney for VISX Corporation, to the European patent office containing applicant's preliminary response to an opposition by Summit Technology, Inc. to European patent application No. 86307420.9–2305/021842.

Paper in European patent application Nos. 86307420.9–2305/0218427 and 87306826.6–2302/0257836 titled "Affidavit of Stephen L. Trokel" Sworn on Dec. 5, 1995.

Form EPO 2042 dated Dec. 29, 1995 having reference No. J.17848 in European patent application No. 86307420.9–2302/0218427.

Facsimile letter dated Feb. 8, 1995 from Howard L. Milhench, attorney for VISX Corporation, to the European patent office containing applicant's preliminary response to (1) an opposition by Firma Carl Zeiss and (2) an opposition by Summit Technology, Inc. to European patent application No. 86304097.8(247260).

Facsimile letter dated Jun. 2, 1994 from Howard L. Milhench, attorney for VISX Corporation, to the European patent office containing VISX's preliminary response to (1) an opposition by Firma Carl Zeiss and (2) an opposition by Summit Technology, Inc. to European patent application No. 87306826.6–2212/0257836.

Letter dated Sep. 22, 1994 from Howard L. Milhench, attorney for VISX Corporation, to the European patent office containing applicant's preliminary response to (1) an opposition by Firma Carl Zeiss and (2) an opposition by Summit Technology, Inc. to European patent application No. 87310283.4–0274205.

Facsimile message dated Dec. 23, 1991 from Howard L. Milhench, attorney for VISX Corporation, to the European patent office containing VISX's observations regarding (1) an opposition by Synthelabo, Paris (FR) and (2) an opposition by Zeiss, Oberkochen (DE) to European patent application No. 896304315.4–2305.

CA 96 N 2351 (Amended Answer and counter claim in Pillar Point partners et al. v. Dishler et al.

CA 96 N 2051, PHX PGR (Amended Answer in Pillar Point Partners et al. v. Dulaney et al.

FTC Docket # 9286, Complaint in the matter of Summit Technology, Inc. and VISX, Inc.

"Front pages of 20 District Court cases involving VISX, Incorporated, the assignee."

Photorefractive Keratectomy: A technique for laser refractive surgery; Munnerlyn, et al., J. Cataract Refract Surg., vol. 14, pp. 46–52 (Jan. 1988).

Application of the excimer laser to area recontouring of the cornea; Yoder, et al., SPIE vol. 1023, Excimer Laser and Applications, pp. 260–267 (1988).

Photorefractive Keratectomy to Create Toric Ablations for Correction of Astigmatism, Arch. Ophthalmol. vol. 109, May, 1991, pp. 700–713, McDonnell et al.

Analysis of an Adjustable Slit Design for Correcting Astigmatism; Clapham, et al., SPIE vol. 1423, Ophthalmic Technologies Jan. 21–22, 1991, Los Angeles, CA.

Photorefractive Keratectomy for Astigmatism: Initial Clinical Results; McDonnell, M.D. et al., Arch of Ophthalmol, vol. 109, Oct. 1991.

Testimony of Richard H. Keates in In re Summit Tech., Inc. et al., No. 9286 (F.T.C.).

Testimony of Stephen L. Trokel in In re Summit Tech., Inc. et al., No. 9286 (F.T.C.).

Expert report of Neal A. Sher, M.D., dated Nov. 2, 1998.

Expert report of Neal A. Sher, M.D., dated Nov. 13, 1998 (different content).

Expert report of Massoud Motamedi, Ph.D., dated Nov. 2, 1998.

George O. Waring III, *Development & Eval. Of Refractice Surgical Procedures* (1987).

Draft article with editor's notes, Stephen L. Trokel et al., Excimer Laser Surgery of the Cornea.

*YAG Laser Ophthalmic Microsurgery,* edited by Stephen L. Trokel, M.D., copyright 1983 by Appleton–Century–Crofts.

METHOD AND APPARATUS FOR COMBINED CYLINDRICAL AND SPHERICAL EYE CORRECTIONS

This is a continuation of application Ser. No. 08/698,971, filed on Aug. 16, 1996; now abandoned, which is a continuation of application Ser. No. 08/138,552, filed on Oct. 15, 1993, now U.S. Pat. No. 5,713, 892 which is a continuation of application Ser. No. 07/746,446, filed on Aug. 16, 1991, now abandoned.

BACKGROUND OF THE INVENTION

This invention relates to ophthalmological surgery techniques which employ an ultraviolet laser used to provide photodecomposition of the surface of the cornea in order to correct vision defects.

Ultraviolet laser based systems and methods are known for enabling ophthalmological surgery on the surface of the cornea in order to correct vision defects by the technique known as ablative photodecomposition. In such systems and methods, the irradiated flux density and exposure time of the cornea to the ultraviolet laser radiation are so controlled as to provide a surface sculpting of the cornea to achieve a desired ultimate surface change in the cornea, all in order to correct an optical defect. Such systems and methods are disclosed in the following U.S. patents and patent applications, the disclosures of which are hereby incorporated by reference: U.S. Pat. No. 4,665,913 issued May 19, 1987 for "METHOD FOR OPHTHALMOLOGICAL SURGERY"; U.S. Pat. No. 4,669,466 issued Jun. 2, 1987 for "METHOD AND APPARATUS FOR ANALYSIS AND CORRECTION OF ABNORMAL REFRACTIVE ERRORS OF THE EYE"; U.S. Pat. No. 4,732,148 issued Mar. 22, 1988 for "METHOD FOR PERFORMING OPHTHALMIC LASER SURGERY"; U.S. Pat. No. 4,770,172 issued Sep. 13, 1988 for "METHOD OF LASER-SCULPTURE OF THE OPTICALLY USED PORTION OF THE CORNEA"; U.S. Pat. No. 4,773,414 issued Sep. 27, 1988 for "METHOD OF LASER-SCULPTURE OF THE OPTICALLY USED PORTION OF THE CORNEA"; U.S. patent application Ser. No. 109,812 filed Oct. 16, 1987 for "LASER SURGERY METHOD AND APPARATUS"; and U.S. patent application Ser. No. 081,986 filed Aug. 5, 1987 for "PHOTOREFRACTIVE KERATECTOMY".

In the above-cited U.S. Pat. No. 4,665,913 several different techniques are described which are designed to effect corrections for specific types of optical errors in the eye. For example, a myopic condition, which is typically caused by excessive curvature in the anterior surface of the cornea, is corrected by laser sculpting the corneal surface to flatten the curvature. In addition, an astigmatic condition, which is typically caused by a cylindrical component of curvature departing from the otherwise generally spherical curvature of the surface of the cornea, is corrected by effecting cylindrical ablation about the axis of cylindrical curvature of the eye. Other optical errors can be corrected in a similar fashion.

The technique for providing the flattening of the corneal curvature for myopia error correction involves selectively varying the area of the cornea exposed to the laser beam radiation to produce an essentially spherical surface profile of reduced curvature. This selective variation of the irradiated area may be accomplished in a variety of ways. U.S. Pat. No. 4,732,148 cited above discloses the technique of providing a movable opaque element having apertures of various diameters and passing the laser beam through different ones of the apertures in a programmed fashion, starting either with a smallest diameter aperture and progressively increasing the surface area of exposure using apertures of wider diameters, or using the reverse process. Another technique for accomplishing varying areal exposure employs a variable diameter iris for controlling the area of the cornea exposed to the laser beam. Still another technique for providing the flattening of the corneal curvature for myopia error correction involves the use of a laser beam attenuator which varies the energy distribution of the laser beam to sculpt the surface of the cornea in conformance with the varied energy distribution. The attenuator typically includes a positive lens-shaped portion with a laser energy absorbing material and end caps having planar outer surfaces and the same refractive index as the positive portion, which prevents refraction of the laser beam upon passing through the attenuator. This technique is disclosed in U.S. Pat. No. 4,838,266, issued Jun. 13, 1989 for "LENS SHAPING DEVICE USING A LASER ATTENUATOR", the disclosure of which is hereby incorporated by reference. The astigmatic cylinder correction is typically performed by providing a pair of movable blades which intercept the laser beam and permit only a rectangular area of the cornea to be exposed to the beam through the width of the slit formed by the confronting edges of the blades, and by controlling the width of the slit in a predetermined manner so that a rectangular area of the cornea of either increasing or decreasing width is exposed to the laser beam. The '466 U.S. patent noted above discloses such a variable width slit mechanism.

In practice, the laser sculpturing ophthalmological surgical system is typically provided with delivery system optics which include both the variable diameter beam shaping element and the variable width slit mechanism in order to afford both myopia and astigmatism corrections. In some patients, there are both myopia and astigmatism defects in the same eye, requiring correction of both errors in order to improve vision. In the past, such compound errors have been corrected in systems having a variable diameter element and a variable width slit mechanism in a sequential fashion, with the astigmatic correction typically being performed first with the slit mechanism, followed by the correction for myopia using the variable diameter element. This has the disadvantage that the length of the operation is maximized, which increases the time that the patient's eye must be completely immobilized. This increases the physical strain and stress on the patient.

In addition, the cylindrical ablations required to correct astigmatic errors normally result in sharp transitions in the cornea at the extreme ends of the sculpted area. It has been observed that the eye responds to such sharp transitions by promoting growth of the epithelium and the stroma to smooth out sharp edges in the surface of the cornea. This has an adverse optical effect, sometimes termed the "hyperopic shift", which causes vision regression and thus reduces the effectiveness of the laser sculpting technique. In addition, such sharp transitions have the potential to induce changes in corneal curvature, such as flattening along the cylindrical axis of ablation. In the past, attempts have been made to reduce the hyperopic shift by laser sculpting smoothing transition zones. This has been accomplished by manipulating the diameter of a circular aperture at the ends of the slit to form sigmoidal or "s" shaped transition zones. However, therapeutic patients undergoing large area ablations questionable since many of such patents still exhibit hyperopic shifts.

SUMMARY OF THE INVENTION

The invention comprises a method and apparatus for providing both spherical myopic and cylindrical astigmatic corrections to the cornea of an eye which eliminates the sharp transitions at the ends of the cylindrical ablation and which reduces the time required to perform both types of optical error correction.

From a method standpoint, the invention comprises the steps of concurrently correcting myopic sphere and astigmatic cylinder errors in an eye by selective ultraviolet radiation and ablative photodecomposition of the corneal surface in a volumetric removal of corneal tissue and with depth penetration into the stroma to effect toric ablation. The toric ablation is effected by passing the ultraviolet radiation in the form of a laser beam through a slit of varying width and an aperture of varying diameter. Preferably, the slit width is varied from a minimum value to a maximum value, while the aperture diameter is contemporaneously varied from a maximum value to a minimum value. The inverse operation of the slit and the aperture is also effective, though less preferred. Alternatively, the toric ablation is effected by passing the ultraviolet radiation in the form of a laser beam through a variable aperture modulator to produce an elliptical beam profile of variable dimensions. The elliptical beam profile is preferably produced in this embodiment by angularly directing the laser beam at a variable aperture element having a plurality of circular apertures of different diameters, and progressively positioning different ones of the apertures into the path of the beam. The laser beam encounters a series of elliptical apertures of varying axial dimension, depending on the tilt angle and the aperture diameter.

In another method aspect, the invention comprises a method of changing the anterior surface of the cornea of an eye from initial spherical and cylindrical curvature having myopic and astigmatic optical properties to a subsequent curvature having correctively improved optical properties, which method comprises exposing the surface of the cornea and passing ultraviolet laser radiation through a variable aperture element to selectively ablate the exposed surface of the cornea by photodecomposition, with penetration into the stroma and substantially simultaneous spherical and cylindrical volumetric scupturing removal of corneal tissue to such penetration depth and profile as to characterize the anterior surface of the cornea with said subsequent curvature.

In a still further aspect of the invention, the invention comprises a method of using an ultraviolet laser to concurrently correct myopic and astigmatic optical errors of an eye, which method comprises the steps of adjusting the intensity of laser beam projection to a level at which laser beam projection onto the exposed surface of the cornea of the eye will result in a corneal tissue ablation per unit time which is a function of a predetermined maximum ablation depth into the stroma of the cornea, and directing the laser beam at the exposed surface of the cornea in a controlled program of circular and rectangular area coverage as a function of time to redefine the exposed surface curvature by volumetric removal of corneal tissue in the course of selective ablative sculpture of the stroma. The step of directing the laser beam at the exposed surface of the cornea is performed by passing the laser beam through an aperture and a slit and varying the diameter of the aperture and the width of the slit to effect toric ablation of the stroma.

For a fuller understanding of the nature and advantages of the invention, reference should be had to the ensuing detailed description taken in conjunction with the accompanying drawings.

DESCRIPTION OF THE PREFERRED EMBODIMENTS

Figure 1:
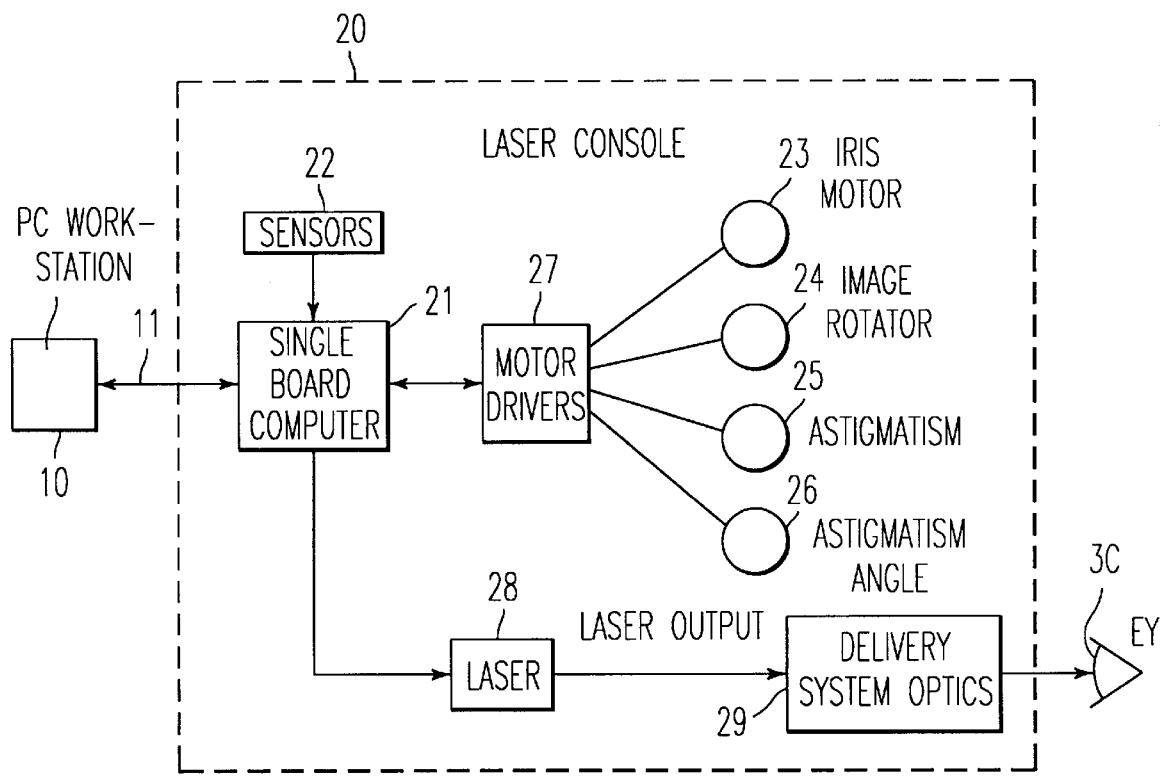
FIG. 1 is a block diagram of an ophthalmological laser surgery system for performing the invention.

Turning now to the drawings, FIG. 1 illustrates a block diagram of an ophthalmological surgery system for performing the invention. As seen in this Fig., a personal computer (PC) work station 10 is coupled to a single board computer 21 of a laser surgery unit 20 by means of a first bus connection 11. PC work station 10 and the subcomponents of laser surgery unit 20 are known components and preferably comprise the elements of the VISX TWENTY/TWENTY EXCIMER LASER SYSTEM available from Visx, Incorporated of Sunnyvale, Calif. Thus, the laser surgery system 20 includes a plurality of sensors generally designated with reference numeral 22 which produce feedback signals from the movable mechanical and optical components in the laser optical system, such as the elements driven by an iris motor 23, an image rotator 24, and astigmatism motor 25 and an astigmatism angle motor 26. The feedback signals from sensors 22 are provided via appropriate signal conductors to the single board computer 21, which is preferably an STD bus compatible single board computer using a type 8031 microprocessor. The single board computer 21 controls the operation of the motor drivers generally designated with reference numeral 27 for operating the elements 23–26. In addition, single board computer 21 controls the operation of the Excimer laser 28, which is preferably an argon-fluorine laser with a 193 nanometer wavelength output designed to provide feedback stabilized fluence of 160 mJoules per $cm^2$ at the cornea at the patient's eye 30 via the delivery system optics generally designated with reference numeral 29. Other ancillary components of the laser surgery system 20 which are not necessary to an understanding of the invention, such as a high resolution microscope, a video monitor for the microscope, a patient eye retention system, and an ablation affluent evacuator/filter, as well as the gas delivery system, have been omitted to avoid prolixity. Similarly, the keyboard, display, and conventional PC subsystem components (e.g., flexible and hard disk drives, memory boards and the like) have been omitted from the depiction of the PC work station 10.

Figure 2:
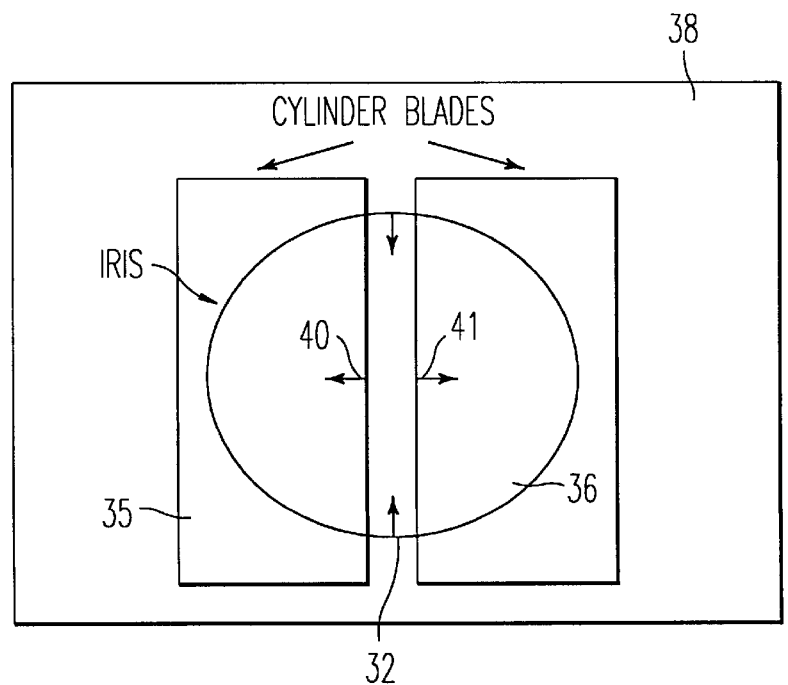
FIG. 2 is a schematic plan view showing the movable slit and variable diameter aperture.

The iris motor 23 is used to control the diameter of a variable diameter iris schematically depicted in FIG. 2. The astigmatism motor 25 is used to control the separation distance between a pair of cylinder blades 35, 36 which are mounted on a platform 38 for bi-directional translatory motion in the direction of arrows 40, 41. Platform 38 is rotatably mounted on a second platform (not illustrated) and is rotationally driven by astigmatism angle motor 26 in a conventional way in order to enable alignment of the slit axis (illustrated in a vertical orientation in FIG. 2) with the cylinder axis of the patient's eye. Iris 32 is driven by iris motor 23 in a known way to change the diameter of the iris opening from a fully opened position (the position illustrated in FIG. 2) to a fully closed position in which the aperture is closed to a minimum diameter of 0.8 mm. It is understood that the variable diameter iris 32 and the cylinder blades 35, 36 are positioned with respect to the output of laser 28 in such a manner as to intercept the beam prior to irradiation of the corneal surface of the patient's eye 30. For the purpose of this application, it may be assumed that iris 32 and cylinder blades 35, 36 are part of the delivery system optics subunit 29 shown in FIG. 1.

Figure 3:
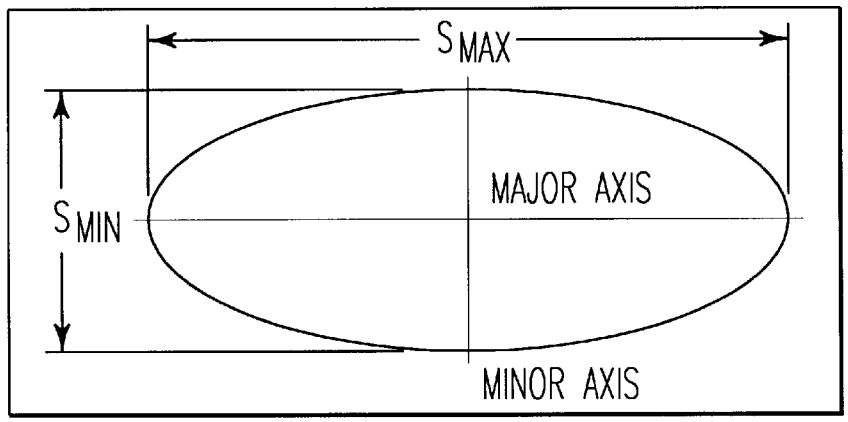
FIG. 3 is a schematic diagram illustrating the geometry of an elliptical ablation.

The system of FIGS. 1 and 2 is used according to the invention to concurrently effect myopic spherical and astigmatic cylindrical corrections to the surface of the cornea by toric ablation. Toric ablation is effected by controlling the combined movement of the cylinder blades 35, 36 and iris 32 over a desired range of movement. The constant depth contour map of a toric ablation consists of a series of concentric ellipses. As seen in FIG. 3, the contour of the outer edge of such an ablation in a flat surface is an ellipse. The ablation geometry along the major and minor axes of the ellipse is spherical, and the ablation has both spherical and cylindrical refractive power.

The refractive power of an elliptcal ablation for treating myopia and myopic cylinder is most easily understood using minus notation for the cylinder. The cylinder axis is located along the major axis of the ellipse, while the refractive power of the cylinder is located along the minor axis. For such an ablation in a flat surface, the spherical refractive power can be calculated from the central depth of ablation, the length of the major axis and the index of refraction of the ablated material. The refractive power along the minor axis can similarly be calculated from the length of the minor axis, the depth of ablation and the index of refraction of the ablated material. The cylindrical power can then be calculated by subtracting the refractive (spherical) power along the major axis from the refractive power along the minor axis. The equations set forth in "Photorefractive keratectomy: A technique for laser refractive surgery" authored by Munnerlyn, et al., J. Cataract Refract Surg-Vol. 18, pages 46–52 (January 1988), the disclosure of which is hereby incorporated by reference, can be used to calculate the ablation geometry in corneal tissue along the major and minor axes of the ellipse. Along the major axis, the length of the major axis, $S_{maj}$, is substituted for the treatment diameter, and the dioptric correction entered into the equations is the spherical correction. To determine the ablation geometry along the minor axis, the sum of the spherical and cylindrical corrections is entered into the equations as the dioptric correction, and the length of the minor axis, $S_{min}$, is substituted for the treatment diameter.

The relative sizes of the major and minor axes will depend upon the ratio of cylindrical to spherical correction. Assuming that the length of the major axis is held constant, the length of the minor axis is approximated by $$S_{min} \sim S_{maj}[D_{cyl}/D_{sph})+1]^{-\frac{1}{2}}$$

In the above equation, $S_{min}$ is the length of the minor axis, $S_{maj}$ the length of the major axis, $D_{cyl}$ the cylindrical correction and $D_{sph}$ the spherical correction. As noted above, this equation assumes minus notation for the cylindrical portion of the correction.

Figure 4:
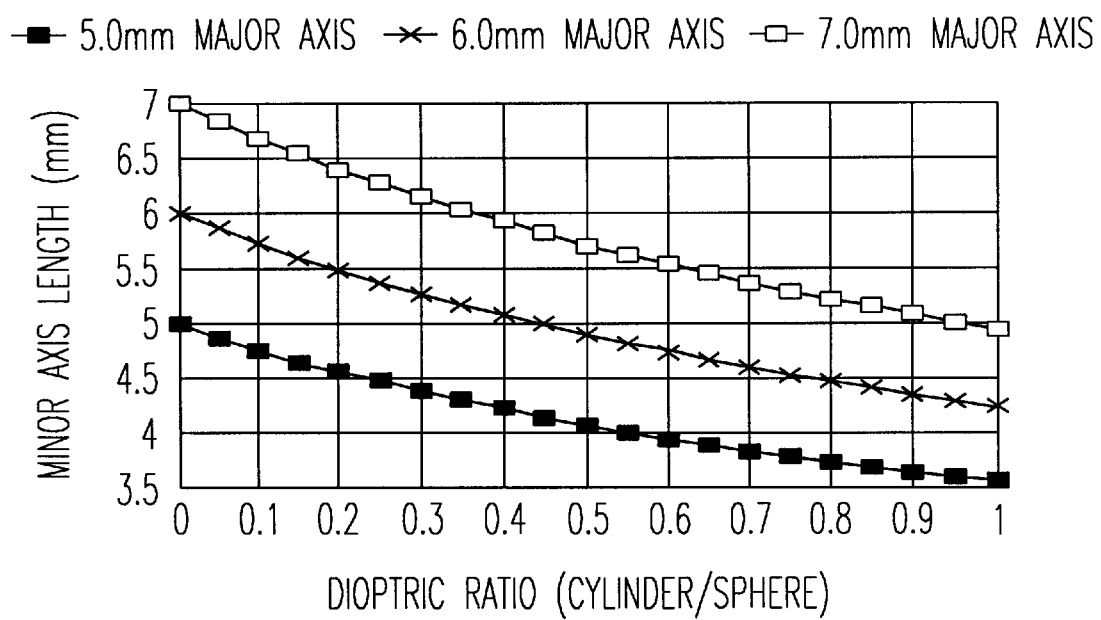
FIG. 4 is a graph showing variation of the minor axis length with correction ratio for different major axis lengths.

To be effective clinically, an elliptical ablation must have a sufficiently large minor axis comparable in size to the maximum diameter of the corneal treatment zone. As shown in FIG. 4, which plots varying ratios of cylindrical to spherical corrections for constant major axis length, there are certain practical limits to the maximum ratio of cylindrical to spherical corrections. In particular, for a given major axis length the length of the minor axis decreases as the ratio of cylindrical to spherical corrections increases. For example, for a major axis of 6.0 mm (corresponding to a laser capable of producing a maximum treatment diameter of 6.0 mm), the minor axis for equal spherical and cylindrical corrections is 4.25 mm. This suggests that the clinical use of toric ablations to correct refractive cylinder should be limited to patients having at least as much spherical error as cylindrical error (for a 6.0 mm maximum treatment diameter). For larger maximum treatment diameters (e.g., the upper curve in FIG. 4 corresponding to a 7.0 mm treatment diameter), the ratio constraints will be different.

Returning to FIG. 2, in the preferred embodiment toric ablations are produced by relative motion of the cylinder blades 35, 36 while varying the diameter of the iris 32. Initially, the cylinder blades 35, 36 are completely closed and the iris 32 is opened to the maximum desired diameter. Thereafter, the cylinder blades 35, 36 are progressively opened while the iris 32 is progressively closed by the respective motors 25, 23. As the cylinder blades 35, 36 are opened, the cylindrical component is ablated in the surface of the cornea. As the diameter of iris 32 is closed contemporaneously with the opening of the cylinder blades 35, 36, the spherical component is ablated in the corneal surface. The combined progressive motion of the cylinder blades 35, 36 and the iris 32 produces the toric ablation desired.

As an example, consider the case of a patient with a refraction of −3.0−2.0×175, average keratometry of 44.5 D and a desired 6.0 mm treatment zone. The iris 32 is initially imaged to a 6.0 mm diameter, and cylinder blades 35, 36 are initially placed in the closed position and rotated to the desired angular orientation in the plane of FIG. 2. Thereafter, as laser 28 is pulsed the cylinder blades 35, 36 are progressively opened to effect a −2.0 D cylindrical correction. At the same time, iris 32 is progressively closed to effect a −3.0 D spherical correction.

The preferred embodiment uses laser 28 to ablate a thin layer of tissue from the surface of the cornea with each pulse. The desired ablation depth along each axis can be predetermined by computer control. The iris 32 is programmed to close at a rate which corresponds to the spherical correction, and the cylindrical blades 35, 36 open at a rate corresponding to the cylindrical correction. The transverse displacement of each aperture between pulses corresponds to the change in desired cut depth for the appropriate aperture (i.e., iris 32 or blades 35, 36). The change in desired cut depth is equal to the amount of material removed with each pulse. Thus, for a −3.0−2.0×175 correction, the iris 32 is closed to create a −3.0 D ablation while the cylinder blades 35, 36 open to create a −2.0 D cylindrical correction. Along the minor axis of the ellipse, the combined effect of the iris 32 and cylinder blades 35, 36 produces a −5.0 D ablation, while the major axis of ellipse has a −3.0 D ablation.

A significant advantage of the preferred embodiment is that the boundaries of the elliptical ablated area are determined by the combined motion of the iris 32 and the cylinder blades 35, 36. As the simultaneous refractive correction proceeds, the intersection of the cylinder blades and iris mark the outer edge of the ablation. The ratio of the minor to major axes is determined by the relative motion of the iris 32 and the cylinder blades 35, 36. Thus, the exact geometry of the ablated area need not be solved for explicitly, and can be varied depending upon the correction required.

Since the number of laser pulses required to effect the spherical correction will usually be greater than the number of laser pulses required to effect the cylindrical correction (assuming equal treatment values of S in the equations of Munnerlyn et al.), cylinder blades 35, 36 will be fully opened to the 6.0 mm position while the iris 32 is not yet fully closed in the above example. Cylinder blades 35, 36 are left at the 6.0 mm position without further movement while the laser finishes the extra pulses required until iris 32 is fully closed. It should be noted that an alternate method of operating the iris 32 and the cylinder blades 35, 36 is to start with the iris 32 initially closed and the cylinder blades 35, 36 initially opened to the maximum slot width, followed by progressive opening of the iris 32 and progressive closing of the blades 35, 36. If the number of pulses required to effect the spherical correction is greater than that required to effect the cylindrical correction (which will be the case whenever the ratio of cylinder-to-sphere shown in FIG. 4 is less than 1.0 and the programmed treatment diameters are equal), motion of blades 35, 36 must be delayed until the extra number of pulses required for the spherical correction have been produced. Otherwise, the blades 35, 36 will be fully closed before the spherical correction is completed. This alternate method of operation thus requires additional capability in the system of FIG. 1 to delay the operation of the astigmatism motor 25 in the closing direction until the extra number of laser pulses required for the spherical correction have been produced.

While the embodiment employing the iris 32 and cylinder blades 35, 36 described above is preferred, the toric ablation may also be effected by employing a variable aperture laser beam modulator to produce an elliptical beam profile of variable dimensions. This may be done by using a mask rotatably mounted in the beam path and having a plurality of variable dimension elliptical apertures with progressive sizes required to produce the desired toric ablation. Alternatively, the mask may have circular apertures of different diameters, and the mask may be positioned at an angle with respect to the laser beam axis so that each circular aperture provides an elliptical profile to the laser beam. The apertured mask is progressively re-positioned between pulses of the laser beam so as to vary the area of the corneal surface exposed to the laser beam from a smallest elliptical area to a largest elliptical area (or the reverse). Care must be taken to ensure that the major axis of each ellipse is collinear with the desired axis of cylindrical ablation throughout the surgery, and this requires precise positioning of the cornea with respect to the elliptical axes. This alternative embodiment has the advantage of employing apertured masks which may already be present in an existing system, such as those shown in the above-referenced U.S. Pat. No. 4,732, 148 (particularly FIGS. 9 and 24).

As will now be apparent, the invention enables both spherical and cylindrical corrections to be concurrently effected to the eye of a patient, thus eliminating the prior need with variable aperture and slit systems to first perform the one type of correction (usually the astigmatic correction using the slit) followed by the other correction (typically the spherical correction using the variable aperture). This reduces the total number of pulses required to effect both types of correction to simply the number required to perform the spherical correction. Since the laser beam cross section and intensity can vary over time and with repeated pulsing, the invention reduces the likelihood of error in effecting the desired contoured shaping of the corneal surface. In addition, by sculpting the corneal surface using a toric ablation, the steep vertical "walls" with depth equal to the astigmatic ablation depth are not formed at each end of the cylindrical ablation: consequently, there is no need to produce the sigmoidal transition zones, which simplifies the procedure. In addition, the absence of any steep edges in the corneal ablation reduces the tendency of the eye to produce excessive growth of the epithelium over the ablated surface and this reduces the hyperopic shift phenomenon.

It is understood that the invention encompasses various techniques used to prepare the anterior surface of the cornea for the laser based ablation. For example, removal of the epithelium by both surgical scraping and peeling to expose the corneal surface, as well as laser ablation of the epithelium prior to or contemporaneously with the laser sculpting of the corneal surface, are encompassed by the invention. Thus, the term "corneal surface" refers to the surface to be sculpted to the desired corrective curvature, regardless of whether or not the epithelium or Bowman's membrane (or both) intervene with the actual corneal surface.

While the above provides a full and complete disclosure of the preferred embodiments of the invention, various modifications, alternate constructions and equivalents may be employed as desired. For example, while the invention has been described with specific reference to the system of FIGS. 1 and 2, other arrangements may be employed to produce the variable rectangular and circular areal irradiation desired. Therefore, the above description and illustrations should not be construed as limiting the invention, which is defined by the appended claims.

What is claimed is:

1. A laser eye surgical system for providing elliptical beam cross-sections for spherical and astigmatic corrections to a cornea of an eye, said system comprising:

(a) a laser for producing a laser beam, said laser positioned so that said laser beam propagates along a beam path;

(b) beam shaping means disposed along said beam path of said laser beam for shaping said laser beam by transmitting only a portion of said laser beam having an elliptical cross-section past said beam shaping means, said beam shaping means comprising a mask having a plurality of elliptical apertures having different dimensions from one another, at least some of said elliptical apertures having different sizes from one another; and (c) means for rotatably mounting said mask so that different ones of said apertures of said mask can be positioned along said beam path at different times, wherein said plurality of apertures are dimensioned to enable producing desired elliptic ablations from corneal tissue.

2. A laser eye surgical system for providing elliptical beam cross-sections for spherical and astigmatic corrections to a cornea of an eye, said system comprising:

(a) a laser for producing a laser beam, said laser positioned so that said laser beam propagates along a beam path;

(b) beam shaping means disposed along said beam path for shaping said laser beam by transmitting only a portion of said laser beam having an elliptical cross-section past said beam shaping means, said beam shaping means comprising
        (i) a mask having an aperture and
        (ii) means for rotating said mask about a mask axis that is perpendicular to said beam path.

3. A system according to claim 2 wherein the eye has an astigmatic axis and said mask axis is perpendicular to said astigmatic axis.

4. A system according to claim 2 wherein said aperture is circular.

5. A system according to claim 2 wherein said mask has a plurality of circular apertures.

6. A system according to claim 2, wherein said means for rotating rotates said mask so that said aperture remains in said beam path.

7. A system for ablating a surface with laser energy, said system comprising:
   (a) means for aligning a surface with a laser which is operable to deliver a beam of photo ablative pulses of laser energy along a path to the surface;
   (b) means for varying a cross-sectional size of the beam by means for shaping the beam into an elliptical form having a major axis and a minor axis, said means for shaping comprising an optical system along said path of the beam, wherein said optical system defines an aperture having a cross-section defining said cross-sectional size of the beam such that the aperture remains in said path while said cross-sectional size varies; and
   (c) means for adjusting said optical system to select an astigmatic ratio of the major axis to the minor axis of the beam on the surface;
   thereby forming a time-varying elliptical distribution of intensity on the surface.

8. The system of claim 7 further comprising means for rotating said optical system to select an orientation of said major axis of the time-varying elliptical distribution of intensity on the surface.

9. The system of claim 7 wherein said means for varying comprises:
   (a) an adjustable aperture and
   (b) means for imaging said adjustable aperture onto the surface.

10. The system of claim 7 further comprising means for adjusting said optical system to select a second astigmatic ratio on the surface.

11. A system for ablating an area of the cornea of an eye for correcting myopic astigmatism, said system comprising:
    (a) means for fixing an eye relative to a laser;
    (b) means for delivering a beam of photo ablative pulses of laser energy from said laser along a path to the cornea;
    (c) an optical system along said path of the beam and comprising means for varying a cross-sectional size of the beam such that the beam passing through said optical system is shaped into an elliptical form having a major axis and a minor axis, wherein said means for varying defines an aperture having a cross-section defining said cross-sectional size of the beam such that the aperture remains in said path while said cross-sectional size varies;
    (d) means for adjusting said optical system to select an astigmatic ratio of the major axis to the minor axis of the beam on the cornea; and
    thereby forming a time-varying generally elliptical distribution of intensity on the cornea.

12. A system claim 11 further comprising means for rotating said optical system to orient the time-varying elliptical distribution of intensity on the cornea.

13. The system claim 11 wherein said optical system comprises:
    (a) an adjustable aperture and
    (b) means for imaging said adjustable aperture onto the cornea.

14. The system of claim 11 further comprising means for adjusting said optical system to define a length of said major axis and thereby selecting the astigmatic ratio of the beam on the cornea.

15. The system of claim 11 wherein said laser is an excimer laser.

16. The system of claim 11 wherein said optical system comprises delivery system optics for transmitting the beam from the laser to the cornea so that the beam has a predetermined fluence at the cornea.

17. A laser system for reprofiling a surface, said laser system comprising:
    (a) an excimer laser for generating pulses of laser light along a beam path and at an energy per pulse such that the pulses impinging onto the surface induce photo ablation of the surface, the laser light having dimensions at the surface;
    (b) beam control means for controlling the dimensions of the laser light to create an astigmatic irradiation pattern at the surface said beam control means comprising:
       (1) two cylinder blades defining a slit shaped aperture and
       (2) an iris, and
       (3) said beam control means disposed along the beam path; and
    (c) adjustment means for shifting said optical means to select an astigmatic ratio for the astigmatic irradiation pattern at the surface.

18. The laser system of claim 17 wherein said excimer laser contains a mixture of gases comprising argon and fluorine for generating 193 nanometer laser radiation.

19. The laser system of claim 17 wherein said iris is an adjustable iris for controlling a diameter of the laser light.

20. The laser system of claim 19 wherein said optical means defines an aperture for controlling the diameter of said laser beam applied to said surface.

21. The laser system of claim 19 wherein said optical means includes means for rotating said cylinder blades to orient an astigmatic axis of the astigmatic irradiation pattern at the surface.

22. The laser system of claim 21 wherein said optical means further comprises delivery system optics.

23. A laser eye surgical system for providing spherical myopic and cylindrical astigmatic corrections to a cornea of an eye, said system comprising:
    (a) a laser for producing a laser beam, said laser positioned so that said laser beam propagates along a beam path;
    (b) beam shaping means disposed along said beam path of said laser beam for shaping said laser beam by transmitting only a portion of said laser beam past said beam shaping means, said beam shaping means comprising
       (i) means for defining a slit shaped aperture having a slit width;
       (ii) means for defining a circular shaped aperture having a circular diameter;
       (iii) means for simultaneously varying said slit width and said circular diameter of said circular shaped aperture.

24. A system according to claim 23 wherein said beam shaping means further comprises means for simultaneously increasing said slit width while decreasing said circular diameter.

25. A system according to claim 23 wherein said beam shaping means further comprises means for simultaneously decreasing said slit width while increasing said circular diameter.

26. A system according to claim 23, wherein
    (a) said means for defining said circular shaped aperture comprises an iris, and
    (b) said means for simultaneously varying said slit width and said circular diameter comprises means for opening and closing said iris.

27. A system according to claim 23 wherein said laser is an excimer laser.

28. A system according to claim 23 wherein said laser is an excimer laser containing a gas mixture substantially comprising argon and fluorine gas for generating 193 nanometer laser radiation.

29. A system according to claim 23 wherein said slit shaped aperture extends in an extending direction and further comprising means for rotating said first cylinder blade and said second cylinder blade to thereby rotate said extending direction.

30. A system according to claim 23 wherein said laser comprises means for producing laser beam pulses having a wavelength of 193 nanometers and a pulse fluence at the cornea that is stabilized by feedback.

31. A system according to claim 23 wherein
   (a) said means for defining said slit shaped aperture comprises a first cylinder blade and a second cylinder blade, said first cylinder blade has a flat first cylinder blade surface, said second cylinder blade has a flat second cylinder blade surface, said flat first cylinder blade surface opposes said flat second cylinder blade surface, said flat first cylinder blade surface is separated from said flat second cylinder blade surface by a separation distance equal to said slit width, and
   (b) said means for varying said slit width comprises means for varying said separation distance by moving said flat first cylinder blade surface and said flat second cylinder blade surface towards and away from one another.

32. A system according to claim 31 wherein said beam shaping means further comprises means for
   (iv) simultaneously increasing said separation distance from a minimum separation distance value to a maximum separation distance value while decreasing said circular diameter from a maximum diameter value to an intermediate diameter value and then
   (v) maintaining said separation distance value at said maximum separation distance value while decreasing said circular diameter from said intermediate diameter value to a minimum diameter value.

33. A system according to claim 32 wherein said minimum separation distance value is zero and said minimum diameter value is zero.

34. A system according to claim 32 wherein said maximum diameter value and said maximum separation distance value are about six millimeters.

35. A system according to claim 31 wherein said beam shaping means further comprises means for
   (iv) maintaining said separation distance at a maximum separation distance value while increasing said circular diameter from a minimum diameter value to an intermediate diameter value and then
   (v) simultaneously decreasing said separation distance from said maximum separation distance value to a minimum separation distance value while increasing said circular diameter from said intermediate diameter value to a maximum diameter value.

36. A system according to claim 35 wherein said minimum separation distance value is zero and said minimum diameter value is zero.

37. A system according to claim 35 wherein said maximum diameter value and said maximum separation distance are about six millimeters.

38. A apparatus for ablating a surface with laser energy, the apparatus comprising:
   (a) a laser operable to deliver a beam of photoablative pulses of laser energy;
   (b) means for aligning a surface with said laser to deliver a beam of photoablative pulses of laser energy along a path to the surface, the beam having a cross-sectional size;
   (c) an optical system disposed along said path, said optical system comprising
      (1) a slit having a width, a major dimension, and an minor dimension and
      (2) an iris having a diameter;
   (d) means for
      (1) sending a photoablative pulse from said laser through said optical system to said surface,
      (2) changing said width and said diameter, and
      (3) sending another photoablative pulse from said laser means through said optical system to said surface.

39. The apparatus of claim 38 further comprising means for rotating said slit to thereby rotate said major axis.

40. The apparatus of claim 38 wherein said means for aligning comprises means for aligning a surface of an eye with said lasser.

41. The method of claim 38 wherein said laser is an excimer laser.

42. A laser system for reprofiling a surface, said laser system comprising:
   (a) laser means for generating pulses of laser light along a beam path and at an energy per pulse such that the pulses impinging onto the surface induce photoablation of the surface, the laser light having dimensions at the surface;
   (b) optical means including a slit having a width and an iris having a diameter disposed along the beam path for adjusting the dimensions of the laser light along one axis for creating an astigmatic irradiation pattern at the surface; and
   (c) adjustment means for shifting said optical means by varying said width of said slit and said diameter of said iris to select an astigmatic ratio for the astigmatic irradiation pattern at the surface.

43. The laser system of claim 42 wherein said optical means includes an aperture for controlling the diameter of said laser beam applied to said surface.

44. The laser system of claim 42 wherein said laser means is an excimer laser.

45. The laser system of claim 44 wherein said excimer laser is an argon fluoride laser.

46. The laser system of claim 42 wherein said optical means includes means for rotating at least one optical element to orient an astigmatic axis of the astigmatic irradiation pattern at the surface.

47. The laser system of claim 46 wherein said optical means further comprises delivery system optics.

48. A method for ablating an area of the cornea of an eye for correcting myopic astigmatism, the method comprising the steps of:
   (a) fixing an eye relative to a laser means;
   (b) delivering a beam of photoablative pulses of laser energy from said laser means along a path to the cornea, the beam having a cross-sectional size;
   (c) disposing an optical system having a slit having a width and an iris having a diameter along the path of the beam such that the beam passing through said optical system is shaped into an elliptical form having a major axis and a minor axis;
   (d) adjusting said optical system by varying said width of said slit and said diameter of said iris to select an astigmatic ratio of the major axis to the minor axis of the beam on the cornea; and (e) operating said laser means while varying the size of the beam to deliver a radiation beam to said optical system, thereby forming a time-varying elliptical distribution of intensity on the cornea.

49. The method of claim 48 further comprising the step of rotating said optical system to orient the time-varying elliptical distribution of intensity on the cornea.

50. The method of claim 48 further comprising the step of imaging an adjustable aperture onto the cornea.

51. The method of claim 48 further comprising the step of adjusting said optical system to define a length of said major axis and thereby selecting the astigmatic ratio of the beam on the cornea.

52. The method of claim 48 wherein said step of delivering comprises delivering pulses from an excimer laser.

53. The method of claim 48 wherein said step of disposing said optical system comprises disposing delivery system optics for transmitting the beam from the laser means to the cornea so that the beam has a predetermined fluence at the cornea.

54. A method for ablating a surface with laser energy, the method comprising the steps of:

(a) aligning a surface with a laser means which is operable to deliver a beam of photoablative pulses of laser energy along a path to the surface, the beam having a cross-sectional size;

(b) disposing an optical system having a slit having a width and an iris having a diameter along the path of the beam such that the beam passing through said optical system is shaped into an elliptical form having a major axis and a minor axis;

(c) adjusting said optical system by varying said width of said slit and said diameter of said iris to select an astigmatic ratio of the major axis to the minor axis of the beam on the surface; and (d) operating said laser means while varying the size of the beam to deliver a radiation beam to said optical system, thereby forming a time-varying elliptical distribution of intensity on the surface.

55. The method of claim 54 wherein the method further comprises the step of rotating said optical system to select the orientation of the time-varying elliptical distribution of intensity on the surface.

56. The method of claim 54 wherein the method further comprises the step of imaging an adjustable aperture onto the surface.

57. The method of claim 54 wherein the method further comprises the step of adjusting said optical system to select a second astigmatic ratio on the surface.

58. A method for ablating a surface with laser energy, the method comprising the steps of:

(a) aligning a surface with a laser means which is operable to deliver a beam of photoablative pulses of laser energy along a path to the surface, the beam having a cross-sectional size;

(b) disposing along said path an optical system comprising
  (1) a slit with a width, a major dimension, and an minor dimension and
  (2) an iris having a diameter;

(c) sending a photoablative pulse from said laser means through said optical system to said surface;

(d) changing said width and said diameter; then (e) sending another photoablative pulse from said laser means through said optical system to said surface.

59. The method of claim 58 further comprising the step of rotating said slit to rotate said major axis.

60. The method of claim 58 wherein said step of aligning comprises aligning a surface of an eye with said laser means.

61. The method of claim 58 wherein said laser means is an excimer laser and said step of sending a photoblative pulse comprises sending an ultraviolet photoblative pulse from said excimer laser.

* * * * *